(12) United States Patent
Tan et al.

(10) Patent No.: US 12,264,126 B1
(45) Date of Patent: Apr. 1, 2025

(54) DEVICE AND METHOD FOR REFINING ETHANOL

(71) Applicants: Beijing Institute of Technology, Beijing (CN); Beijing University of Chemical Technology, Beijing (CN)

(72) Inventors: Xinyi Tan, Beijing (CN); Qunsheng Li, Beijing (CN); Tianwei Tan, Beijing (CN); Hongkang Zhao, Beijing (CN)

(73) Assignees: Beijing Institute of Technology, Beijing (CN); Beijing University of Chemical Technology, Beijing (CN)

( * ) Notice: Subject to any disclaimer, the term of this patent is extended or adjusted under 35 U.S.C. 154(b) by 0 days.

(21) Appl. No.: 18/963,493

(22) Filed: Nov. 28, 2024

(30) Foreign Application Priority Data

May 13, 2024 (CN) .......................... 202410585790.8

(51) Int. Cl.
| | |
|---|---|
| *C07C 29/78* | (2006.01) |
| *B01D 3/00* | (2006.01) |
| *B01J 19/00* | (2006.01) |
| *C07C 29/76* | (2006.01) |
| *C07C 29/80* | (2006.01) |

(52) U.S. Cl.
CPC .............. *C07C 29/78* (2013.01); *B01D 3/001* (2013.01); *B01J 19/0013* (2013.01); *C07C 29/76* (2013.01); *C07C 29/80* (2013.01)

(58) Field of Classification Search
CPC ................................................ C07C 29/74–80
See application file for complete search history.

(56) References Cited

FOREIGN PATENT DOCUMENTS

CN 110452092 A 11/2019

OTHER PUBLICATIONS

Machine translation of Patent No. CN110452092A, Nov. 15, 2019; pp. 1-14 (Year: 2019).*
CNIPA, Notification of First Office Action for Chinese application CN202410585790.8, Jun. 14, 2024.
CNIPA, Notification to grant patent right for Chinese application CN202410585790.8, Jul. 24, 2024.

* cited by examiner

*Primary Examiner* — Medhanit W Bahta
(74) *Attorney, Agent, or Firm* — Hemisphere Law, PLLC; Zhigang Ma

(57) ABSTRACT

A device for refining ethanol is disclosed, which includes a fermentation unit, a low-pressure column, a medium-pressure column, a high-pressure column and a membrane separation unit. A method for refining ethanol is disclosed, which specifically includes the following steps: after fermenting the biomass feedstock, feeding fermented mash into a low-pressure column and a high-pressure column which are connected in parallel for refining, mixing two column top distillates, and feeding the mixed column top distillates into a medium-pressure column for further rectification; and purifying the refined ethanol vapor with higher purity obtained after rectification in the medium-pressure column by a membrane separation unit to obtain high-concentration ethanol product vapor. The disclosure couples the differential pressure rectification and the membrane separation unit, adjusts the energy network structure, greatly reduces the vapor usage amount of the whole system, and has the advantages of good separation effect, high product quality and the like.

5 Claims, 1 Drawing Sheet

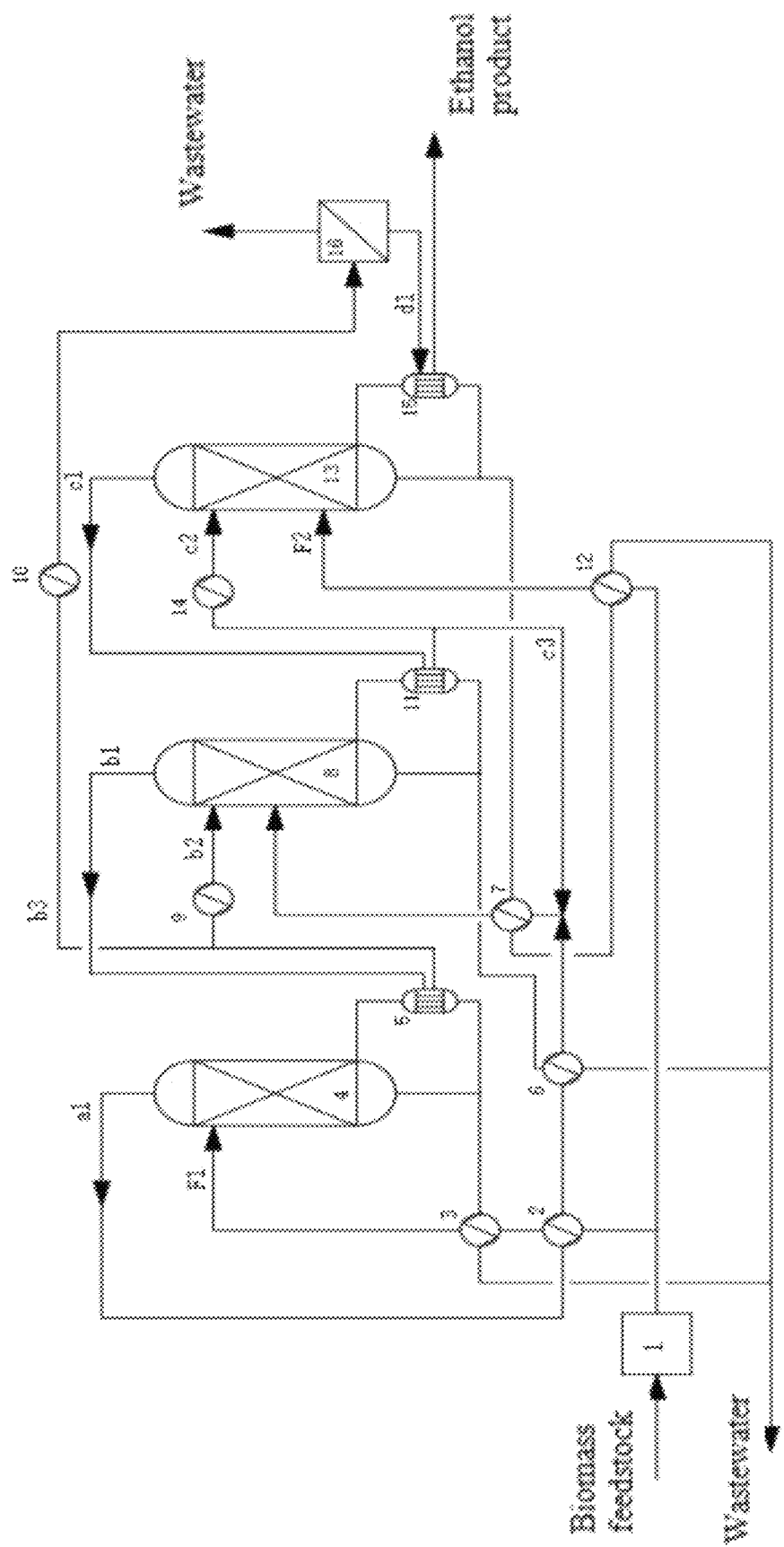

DEVICE AND METHOD FOR REFINING ETHANOL

TECHNICAL FIELD

The disclosure relates to the technical field of chemical production, in particular to a device and a method for refining ethanol.

BACKGROUND ART

The development and utilization of traditional fossil energy is facing serious environmental pollution and resource depletion problems. The fuel ethanol is a green low-carbon renewable energy source, and can be used as a novel energy source for reducing environmental pollution and replacing petroleum fuel. The fuel ethanol is absolute ethanol with the volume concentration of more than 99.5%, has good compatibility with gasoline, and therefore, has been used as a gasoline additive and has wide market prospect. The ethanol gasoline can effectively reduce the emission of harmful substances in automobile exhaust, improve the air quality, help solve the problems of atmospheric environmental pollution and the like, and simultaneously relieve the dependence on traditional fossil energy, which has important strategic significance for sustainable development of national economy.

At present, the mature ethanol dehydration methods include azeotropic distillation, salt extraction distillation, adsorption dehydration and the like, but these methods have high energy consumption and are not beneficial to the refining of high-concentration ethanol.

Therefore, it is an urgent problem to be solved by those skilled in the art to perform adjustment on an original production device so as to reduce the energy consumption of a rectification unit to achieve the purpose of cost reduction and efficiency improvement.

SUMMARY

In view of the above, the present disclosure aims to provide a device and a method for refining ethanol, so as to solve the problems of high energy consumption and low separation efficiency in the ethanol production and refining process.

In order to achieve the above purpose, the present disclosure adopts the following technical schemes:

A device for refining ethanol includes a fermentation unit, a low-pressure column, a medium-pressure column, a high-pressure column and a membrane separation unit;

the fermentation unit is respectively connected with a low-pressure column primary preheater and a high-pressure column preheater through pipelines, and the low-pressure column primary preheater is connected and communicated with the low-pressure column secondary preheater through pipelines;

the low-pressure column is connected with the low-pressure column secondary preheater, a top of the low-pressure column is sequentially connected with the low-pressure column primary preheater and a medium-pressure column primary preheater through pipelines, and the low-pressure column is sequentially connected and communicated with a low-pressure column bottom reboiler and the low-pressure column secondary preheater through pipelines;

the medium-pressure column is connected with a medium-pressure column secondary preheater, a top of the medium-pressure column is sequentially connected with a low-pressure column bottom reboiler, a medium-pressure column auxiliary condenser, a membrane evaporator and the membrane separation unit through pipelines, and the medium-pressure column is sequentially connected and communicated with a medium-pressure column bottom reboiler and the medium-pressure column primary preheater through pipelines;

the high-pressure column is connected with a high-pressure column preheater, a top of the high-pressure column is sequentially connected with the medium-pressure column bottom reboiler, a high-pressure column auxiliary condenser and the medium-pressure column secondary preheater through pipelines, and the high-pressure column is sequentially connected and communicated with the high-pressure column bottom reboiler, the medium-pressure column secondary preheater and the high-pressure column preheater through pipelines; and the membrane separation unit is connected with the high-pressure column bottom reboiler.

Further, the low-pressure column, the medium-pressure column and the high-pressure column are all plate columns or packed columns.

Further, a vapor permeable membrane of the membrane separation unit is an inorganic molecular sieve or polyimide fiber membrane, and the two membranes are particularly suitable for organic solvent dehydration.

The beneficial effect of using the described further solutions lies in that the membrane separation unit of the present disclosure uses a vapor permeable membrane, and has the advantages of simple operation, high separation efficiency, high automation degree, low requirements for the use conditions of the device, no introduction of a third component, low pollution to the environment and the like. Compared with other technologies, the present disclosure has obvious advantages, and at the same time, the energy consumption of the system is reduced significantly, the production cost of the enterprise is reduced, and the economic benefit of the enterprise is greatly improved.

The method for refining ethanol adopts the above refining device and specifically includes the following steps:

(1) performing fermentation on a biomass feedstock by the fermentation unit to obtain a fermented mash, dividing same into two streams, performing pre-heating one stream of the mash by the low-pressure column secondary preheater, and then feeding same into the low-pressure column; performing pre-heating the other stream of the mash by the high-pressure column, and then feeding same directly into the high-pressure column; wherein the low-pressure column and the high-pressure column are connected in parallel in the material flow direction;

(2) after feeding the mash into the low-pressure column for stripping, obtaining a column top low-concentration ethanol vapor, performing heat exchange by the low-pressure column primary preheater, performing pre-heating by the medium-pressure column primary preheater and the medium-pressure column secondary preheater, and feeding same into the medium-pressure column for rectification; discharging the obtained column wastewater out of the system after being subjected to heat exchange by the low-pressure column secondary preheater;

(3) after feeding the mash into the high-pressure column for rectification, obtaining a column top high-concentration ethanol vapor, performing heat exchange by the medium-pressure column bottom reboiler, condensing part of the high-concentration ethanol vapor by the high-pressure column auxiliary condenser and then refluxing same to the high-pressure column, mixing the other part of the high-concentration ethanol vapor with the column top low-concentration ethanol vapor of the low-pressure column having been subjected to heat exchange, preheating same by the medium-pressure column secondary preheater and then feeding same into the medium-pressure column; discharging the obtained column wastewater out of the system after being subjected to heat exchange by the medium-pressure column secondary preheater and the high-pressure column preheater;

(4) obtaining a refined ethanol vapor at the top of the medium-pressure column, performing heat exchange by the low-pressure column bottom reboiler, condensing part of the refined ethanol vapor by the medium-pressure column auxiliary condenser and then refluxing same to the medium-pressure column, and feeding the other part of the refined ethanol vapor into the membrane separation unit after being preheated by the membrane evaporator; discharging an obtained column wastewater out of the system after being subjected to heat exchange by the medium-pressure column primary preheater;

(5) performing a purification on the refined ethanol vapor by the membrane separation unit to obtain an ethanol product vapor, and performing heat exchange on same by the high-pressure column bottom reboiler to obtain an ethanol product; discharging a wastewater obtained by purification out of the system.

Further, in the step (1), the biomass material is at least one of agricultural straw, fungus grass, cellulose, starch, corn and cassava, and preferably cellulose.

Further, in the step (1), the fermentation includes pulverization, saccharification and steaming; the temperature of the fermentation is 35° C.

Further, in the step (1), the mass fraction of ethanol in the fermented mash is 1.5%-10%, preferably 8%.

Further, the absolute pressures at the top and bottom of the low-pressure column, medium-pressure column, and high-pressure column are respectively 0.02-0.08 MPa, 0.10-0.65 MPa, and 0.55-0.85 MPa, and preferably 0.03 MPa and 0.05 MPa, 0.20 MPa and 0.52 MPa and 0.56 MPa and 0.68 MPa respectively; the temperatures at the top of the low-pressure column, medium-pressure column, and high-pressure column are respectively 46-75° C., 80-115° C., and 122-140° C., and preferably 65° C., 85° C. and 122° C. respectively; temperatures at the bottom of the low-pressure column, medium-pressure column, and high-pressure column are respectively 61-94° C., 100-135° C., and 127-145° C., and preferably 80° C., 110° C. and 135° C. respectively.

Further, the reflux volume ratios of column top ethanol vapor at the top of the medium-pressure column and high-pressure column are respectively 1.1-5 and 1.1-8.2, and preferably 1.3 and 1.8 respectively; the column top refined ethanol vapor of the medium-pressure column exchanges heat with the low-pressure column bottom reboiler, the column top high-concentration ethanol vapor of the high-pressure column exchanges heat with the medium-pressure column bottom reboiler, and the ethanol vapor obtained by the membrane separation unit exchanges heat with the high-pressure column bottom reboiler.

Further, in the step (5), the temperature of the purification is 115° C., and a purification time is 120 min.

According to the above technical schemes, compared with the prior art, the disclosure has the following beneficial effects:

1. According to the disclosure, the differential pressure column rectification and the membrane separation are used for separation and purification, the ethanol production route is short, the operation is simple, the cost is low, the environment is protected, the energy is saved, the safety coefficient is higher, the production efficiency and the personnel safety are improved, and the enterprise benefit is remarkably improved.
2. According to the disclosure, only a small amount of external heat source is needed, the bottom reboilers exchange heat with the column top vapor, the column wastewater exchanges heat with the preheater, the waste heat of the rectification unit is integrated and utilized, an energy coupling utilization network is constructed, and the target product yield is improved.
3. The disclosure couples the differential pressure rectification and the membrane separation unit, adjusts the energy network structure, greatly reduces the vapor usage amount of the whole system, and has the advantages of good separation effect, high product quality, short production route, simple operation, small environmental pollution, high resource utilization rate and the like, and the process flow is easy for industrialized production.
4. The disclosure can fully utilize the heat of materials by coupling continuous rectification and membrane separation technology on the basis of meeting the purity of the ethanol product, further reduce the production energy consumption, greatly reduce the production cost, improve the ethanol separation efficiency, increase the product yield and improve the economic benefit.
5. The present disclosure enhances processes such as heat exchange and separation, which can fully reduce production energy consumption and achieve cost reduction and efficiency improvement.
6. The disclosure carries out heat coupling on the inside of differential pressure rectification and the rectification and membrane separation unit, which integrates the heat of the system and reduces the energy consumption.
7. The disclosure is suitable for refining ethanol products such as fuel ethanol, food grade ethanol, medical ethanol, industrial ethanol and the like.

BRIEF DESCRIPTION OF THE DRAWINGS

In order to more clearly illustrate the embodiments of the present disclosure or the technical solutions in the prior art, the drawings that are required to be used in the embodiments or the description of the prior art will be briefly described below, and it is obvious that the drawings in the following description are only embodiments of the present disclosure, and that other drawings can be obtained according to the provided drawings without inventive effort for a person skilled in the art.

FIG. 1 is a schematic structural diagram of a device for refining ethanol and a process flow chart of a method for refining ethanol provided by the disclosure.

Wherein, 1—fermentation unit, 2—low-pressure column primary preheater, 3—low-pressure column secondary preheater, 4—low-pressure column, 5—low-pressure column bottom reboiler, 6—medium-pressure column primary preheater, 7—medium-pressure column secondary preheater, 8—medium-pressure column, 9—medium-pressure column auxiliary condenser, 10—membrane evaporator, 11—medium-pressure column bottom reboiler, 12—high-pressure column preheater, 13—high-pressure column, 14—high-pressure column auxiliary condenser, 15—high-pressure column bottom reboiler, 16—membrane separation unit;

F1~2—fermented mash, a1—low-concentration ethanol vapor, b1~3—refined ethanol vapor, c1~3—high-concentration ethanol vapor, d1—ethanol product vapor.

DETAILED DESCRIPTION OF THE EMBODIMENTS

Embodiments of the present disclosure are described in detail below, examples of which are illustrated in the accompanying drawings, wherein like or similar reference numerals refer to like or similar elements or elements having like or similar functions throughout. The embodiments described below by referring to the drawings are illustrative and intended to explain the present disclosure and should not be construed as limiting the disclosure.

In the description of the present disclosure, it should be understood that the terms "upper", "lower", "front", "rear", "left", "right", "vertical", "horizontal", "top", "bottom", "inner", "outer", etc. indicate orientations or positional relationships based on the drawings, are merely for convenience in describing the present disclosure and simplifying the description, and do not indicate or imply that the units or elements referred to must have a specific orientation, be configured and operated in a specific orientation, and thus should not be construed as limiting the present disclosure.

Furthermore, the terms "first," "second," and the like, are used for descriptive purposes only and are not to be construed as indicating or implying a relative importance or implicitly indicating the number of technical features indicated. Thus, a feature defining "a first" or "a second" may explicitly or implicitly include one or more such feature. In the description of the present disclosure, the meaning of "a plurality" is two or more, unless explicitly defined otherwise.

In the present disclosure, unless explicitly specified and limited otherwise, the terms "mounted," "connected," "secured," and the like are to be construed broadly, and may be, for example, fixedly connected, detachably connected, or integrally formed; can be mechanically or electrically connected; can be directly connected or indirectly connected through an intermediate medium, and can be communicated with the inside of two elements or the interaction relationship of the two elements. The specific meaning of the above terms in the present disclosure can be understood by those of ordinary skill in the art according to the specific circumstances.

In the present disclosure, unless explicitly specified or limited otherwise, a first feature "above" or "below" a second feature may include both the first and second features being in direct contact, as well as the first and second features not being in direct contact but being in contact with each other through additional features therebetween. Moreover, a first feature being "above," "over" and "on" a second feature includes the first feature being directly above and obliquely above the second feature, or simply indicating that the first feature is higher in level than the second feature. The first feature being "under", "below" and "beneath" the second feature includes the first feature being directly under and obliquely below the second feature, or simply means that the first feature is less level than the second feature.

The embodiment of the disclosure provides a device for refining ethanol, which is shown in FIG. 1 and includes a fermentation unit 1, a low-pressure column 4, a medium-pressure column 8, a high-pressure column 13 and a membrane separation unit 16.

The fermentation unit 1 is respectively connected with a low-pressure column primary preheater 2 and a high-pressure column preheater 12 through pipelines, and the low-pressure column primary preheater 2 is connected and communicated with the low-pressure column secondary preheater 3 through pipelines.

The low-pressure column 4 is connected with the low-pressure column secondary preheater 3, a top of the low-pressure column 4 is sequentially connected with the low-pressure column primary preheater 2 and a medium-pressure column primary preheater 6 through pipelines, and the low-pressure column 4 is sequentially connected and communicated with a low-pressure column bottom reboiler 5 and the low-pressure column secondary preheater 3 through pipelines.

The medium-pressure column 8 is connected with a medium-pressure column secondary preheater 7, a top of the medium-pressure column 8 is sequentially connected with a low-pressure column bottom reboiler 5, a medium-pressure column auxiliary condenser 9, a membrane evaporator 10 and the membrane separation unit 16 through pipelines, and the medium-pressure column 8 is sequentially connected and communicated with a medium-pressure column bottom reboiler 11 and the medium-pressure column primary preheater 6 through pipelines.

The high-pressure column 13 is connected with a high-pressure column preheater 12, a top of the high-pressure column 13 is sequentially connected with the medium-pressure column bottom reboiler 11, a high-pressure column auxiliary condenser 14 and the medium-pressure column secondary preheater 7 through pipelines, and the high-pressure column 13 is sequentially connected and communicated with the high-pressure column bottom reboiler 15, the medium-pressure column secondary preheater 7 and the high-pressure column preheater 12 through pipelines.

The membrane separation unit 16 is connected with the high-pressure column bottom reboiler 15.

In one embodiment, low-pressure column 4, medium-pressure column 8, and high-pressure column 13 are all plate columns. In another embodiment, low-pressure column 4, medium-pressure column 8 and high-pressure column 13 are all packed columns.

In one embodiment, a vapor permeable membrane of the membrane separation unit 16 is an inorganic molecular sieve. In another embodiment, a vapor permeable membrane of the membrane separation unit 16 is a polyimide fiber membrane.

Example 1

The method for refining ethanol (a 30,000 tons/year cellulosic fuel ethanol project) using the above device for refining ethanol, as shown in FIG. 1, specifically includes the following steps.

(1) A fermentation is performed on a biomass feedstock by the fermentation unit 1 to obtain a fermented mash, and the fermented mash is divided into two streams. A pre-heating is performed on one stream of the mash by the low-pressure column secondary preheater 3, and then the same is fed into the low-pressure column 4. A pre-heating is performed on the other stream of the mash by the high-pressure column preheater, and then the same are directly fed into the high-pressure column 13. The low-pressure column and the high-pressure column are connected in parallel in the material flow direction.

Wherein, the biomass feedstock is cellulose; the fermentation includes pulverization, saccharification and steaming; a temperature of the fermentation is 35° C.; a mass fraction of ethanol in the fermented mash is 8%.

(2) The mash is fed into the low-pressure column 4 for stripping to obtain a column top low-concentration ethanol vapor, and the low-concentration ethanol vapor enters the medium-pressure column 8 for rectification after heat exchange by the low-pressure column primary preheater 2 and pre-heating by the medium-pressure column primary preheater 6 and the medium-pressure column secondary preheater 7. The obtained column wastewater is discharged out of the system after being subjected to heat exchange by the low-pressure column secondary preheater 3.

Wherein, the low-pressure column 4 is a packed column, the column top temperature is 65° C., the column bottom temperature is 80° C., the absolute pressure at the column top and the column bottom is 0.03 MPa and 0.05 MPa respectively, the mass fraction of low-concentration ethanol vapor at the column top is 25%, and the column components exchange heat with the column top refined ethanol vapor of the medium-pressure column 8 and then return to the low-pressure column 4 for recycle of the ethanol components.

(3) The mash is fed into the high-pressure column 13 for rectification to obtain column top high-concentration ethanol vapor, heat exchange is performed by the medium-pressure column bottom reboiler 11, one part of the high-concentration ethanol vapor is condensed by the high-pressure column auxiliary condenser 14 and then flows back to the high-pressure column 13, the other part of the high-concentration ethanol vapor is mixed with the column top low-concentration ethanol vapor of the low-pressure column 4 after heat exchange, and the mixture is preheated by the medium-pressure column secondary preheater 7 and then enters the middle-pressure column 8; the obtained column wastewater is discharged out of the system after being subjected to heat exchange by the high-pressure column preheater 12.

Wherein, the high-pressure column 13 is a packed column, the column top temperature is 122° C., the column bottom temperature is 135° C., the reflux volume ratio is 1.8, the absolute pressures at the column top and the column bottom are respectively 0.56 MPa and 0.68 MPa, the mass fraction of column top high-concentration ethanol vapor is 81%, and the column components exchange heat with the ethanol product vapor obtained by the membrane separation unit 16 and then return to the high-pressure column 13 for recycle of the ethanol components.

(4) The refined ethanol vapor is obtained at the top of the medium-pressure column 8, heat exchange is performed by the low-pressure column bottom reboiler 5, one part of the refined ethanol vapor is condensed by the medium-pressure column auxiliary condenser 9 and is refluxed to the medium-pressure column 8, and the other part of the refined ethanol vapor is preheated by the membrane evaporator 10 and then enters the membrane separation unit 16; the obtained column wastewater is discharged out of the system after being subjected to heat exchange by the medium-pressure column primary preheater 6.

Wherein, the medium-pressure column 8 is a packed column, the column top temperature is 85° C., the column bottom temperature is 110° C., the reflux volume ratio is 1.3, the absolute pressure at the column top and the column bottom is 0.20 MPa and 0.52 MPa respectively, the mass fraction of the column top refined ethanol vapor is 92%, and the column components exchange heat with the column top high-concentration ethanol vapor of the high-pressure column 13 and then return to the medium-pressure column 8 for recycle of the ethanol components.

(5) A purification is performed on the refined ethanol vapor by the membrane separation unit 16 to obtain ethanol product vapor, and the heat exchange is performed by the high-pressure column bottom reboiler 15 to obtain an ethanol product; the wastewater obtained by purification is discharged out of the system.

Wherein, the membrane separation unit 16 is at normal pressure, the vapor permeable membrane is an inorganic molecular sieve, the purification temperature is 115° C., the time is 120 min, and the mass fraction of the ethanol product vapor and the ethanol product is 99.99%.

In the description of the present specification, a description referring to terms "one embodiment," "some embodiments," "examples," "specific examples," or "some examples," etc., means that a particular feature, structure, material, or characteristic described in connection with the embodiment or example is included in at least one embodiment or example of the present disclosure. In this specification, schematic representations of the above terms are not necessarily directed to the same embodiment or example. Furthermore, the particular features, structures, materials, or characteristics described may be combined in any suitable manner in any one or more embodiments or examples. Further, one skilled in the art can engage and combine the different embodiments or examples described in this specification.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A device for refining ethanol, comprising a fermentation unit, a low-pressure column, a medium-pressure column, a high-pressure column and a membrane separation unit;

the fermentation unit is respectively connected with a low-pressure column primary preheater and a high-pressure column preheater through pipelines, and the low-pressure column primary preheater is connected and communicated with a low-pressure column secondary preheater through pipelines;

the low-pressure column is connected with the low-pressure column secondary preheater, a top of the low-pressure column is sequentially connected with the low-pressure column primary preheater and a medium-pressure column primary preheater through pipelines, and the low-pressure column is sequentially connected and communicated with a low-pressure column bottom reboiler and the low-pressure column secondary preheater through pipelines;

the medium-pressure column is connected with a medium-pressure column secondary preheater, a top of the medium-pressure column is sequentially connected with a low-pressure column bottom reboiler, a medium-pressure column auxiliary condenser, a membrane evaporator and the membrane separation unit through pipelines, and the medium-pressure column is sequentially connected and communicated with a medium-pressure column bottom reboiler and the medium-pressure column primary preheater through pipelines;

the high-pressure column is connected with a high-pressure column preheater, a top of the high-pressure column is sequentially connected with the medium-pressure column bottom reboiler, a high-pressure column auxiliary condenser and the medium-pressure column secondary preheater through pipelines, and the high-pressure column is sequentially connected and communicated with the high-pressure column bottom reboiler, the medium-pressure column secondary preheater and the high-pressure column preheater through pipelines;

the membrane separation unit is connected with the high-pressure column bottom reboiler;

the low-pressure column, the medium-pressure column and the high-pressure column are all plate columns or packed columns;

a vapor permeable membrane of the membrane separation unit is an inorganic molecular sieve or polyimide fiber membrane.

2. A method for refining ethanol, wherein the device for refining ethanol according to claim 1 is used, comprising the following steps:

(1) performing fermentation on a biomass feedstock by the fermentation unit to obtain a fermented mash, dividing same into two streams, performing pre-heating on one stream of the mash by the low-pressure column secondary preheater, then feeding same into the low-pressure column; performing pre-heating the other stream of the mash by the high-pressure column preheater, and then feeding same directly into the high-pressure column; wherein the low-pressure column and the high-pressure column are connected in parallel in a material flow direction;

(2) after feeding the mash into the low-pressure column for stripping, obtaining a column top low-concentration ethanol vapor, performing heat exchange by the low-pressure column primary preheater, performing pre-heating by the medium-pressure column primary preheater and the medium-pressure column secondary preheater, and feeding same into the medium-pressure column for rectification; discharging an obtained column wastewater out of the system after being subjected to heat exchange by the low-pressure column secondary preheater;

(3) after feeding the mash into the high-pressure column for rectification, obtaining a column top high-concentration ethanol vapor, performing heat exchange by the medium-pressure column bottom reboiler, condensing part of the high-concentration ethanol vapor by the high-pressure column auxiliary condenser and then refluxing same to the high-pressure column, mixing the other part of the high-concentration ethanol vapor with the column top low-concentration ethanol vapor of the low-pressure column having been subjected to heat exchange, preheating the mixture by the medium-pressure column secondary preheater and then feeding same into the medium-pressure column; discharging an obtained column wastewater out of the system after being subjected to heat exchange by the medium-pressure column secondary preheater and the high-pressure column preheater;

(4) obtaining a refined ethanol vapor at the top of the medium-pressure column, performing heat exchange by the low-pressure column bottom reboiler, condensing part of the refined ethanol vapor by the medium-pressure column auxiliary condenser and then refluxing same to the medium-pressure column, and feeding the other part of the refined ethanol vapor into the membrane separation unit after being preheated by the membrane evaporator; discharging an obtained column wastewater out of the system after being subjected to heat exchange by the medium-pressure column primary preheater;

(5) performing a purification on the refined ethanol vapor by the membrane separation unit to obtain an ethanol product vapor, and performing heat exchange on same by the high-pressure column bottom reboiler to obtain an ethanol product; discharging a wastewater obtained by purification out of the system;

wherein, absolute pressures at the top and bottom of the low-pressure column, medium-pressure column, and high-pressure column are respectively 0.02-0.08 MPa, 0.10-0.65 MPa, and 0.55-0.85 MPa; temperatures at the top of the low-pressure column, medium-pressure column, and high-pressure column are respectively 46-75° C., 80-115° C., and 122-140° C.; temperatures at the bottom of the low-pressure column, medium-pressure column, and high-pressure column are respectively 61-94° C., 100-135° C., and 127-145° C.;

reflux volume ratios of column top ethanol vapor at the top of the medium-pressure column and high-pressure column are respectively 1.1-5 and 1.1-8.2;

a temperature of the purification is 115° C., and a duration is 120 min.

3. The method for refining ethanol according to claim 2, wherein in the step (1), the biomass material is at least one of agricultural straw, fungus grass, cellulose, starch, corn and cassava.

4. The method for refining ethanol according to claim 2, wherein in the step (1), the fermentation comprises pulverization, saccharification and steaming; a temperature of the fermentation is 35° C.

5. The method for refining ethanol according to claim 2, wherein in the step (1), a mass fraction of ethanol in the fermented mash is 1.5%-10%.

* * * * *